(12) United States Patent
Yin et al.

(10) Patent No.: US 9,359,642 B2
(45) Date of Patent: Jun. 7, 2016

(54) METHOD FOR PREPARING NUCLEIC ACID LIBRARY, ITS USES AND KITS

(71) Applicants: BGI Shenzhen Co., Limited, Shenzhen (CN); BGI Shenzhen, Shenzhen (CN)

(72) Inventors: Xuyang Yin, Shenzhen (CN); Chunlei Zhang, Shenzhen (CN); Hui Jiang, Shenzhen (CN); Xiuqing Zhang, Shenzhen (CN); Shengpei Chen, Shenzhen (CN)

(73) Assignees: BGI SHENZHEN CO., LIMITED, Shenzhen (CN); BGI SHENZHEN, Shenzhen (CN)

( * ) Notice: Subject to any disclaimer, the term of this patent is extended or adjusted under 35 U.S.C. 154(b) by 5 days.

(21) Appl. No.: 14/352,492

(22) PCT Filed: Oct. 16, 2012

(86) PCT No.: PCT/CN2012/083036
§ 371 (c)(1),
(2) Date: Apr. 17, 2014

(87) PCT Pub. No.: WO2013/056640
PCT Pub. Date: Apr. 25, 2013

(65) Prior Publication Data
US 2014/0296084 A1    Oct. 2, 2014

(30) Foreign Application Priority Data
Oct. 18, 2011  (CN) .......................... 2011 1 0316066

(51) Int. Cl.
*C12Q 1/68* (2006.01)
*C12N 15/10* (2006.01)

(52) U.S. Cl.
CPC .......... *C12Q 1/6874* (2013.01); *C12N 15/1093* (2013.01); *C12Q 1/686* (2013.01); *C12Q 1/6853* (2013.01); *C12Q 1/6869* (2013.01)

(58) Field of Classification Search
None
See application file for complete search history.

(56) References Cited

U.S. PATENT DOCUMENTS

2007/0128624 A1* 6/2007 Gormley .............. C12Q 1/6855
435/6.12

FOREIGN PATENT DOCUMENTS

WO   WO 2014031954 A1 *  2/2014 ........... C12Q 1/6855

OTHER PUBLICATIONS

Grothues et al. Nucleic Acids Research (1993) 21: 1321-1322.*
Parameswaran et al. Nucleic Acids Research (2007) 35: e130.*
Weise et al. European Journal of Human Genetics, 2010, 18: 457-462 + Supplementary Information (six pages).*
Kim et al. Journal of Surgical Oncology, 2007, 96: 429-435.*
Okamoto, A. Organic and Biomolecular Chemistry, 2009, 7: 21-26.*
Darst et al. Current Protocols in Molecular Biology, 2010, Chapter 7, Unit 7.9, 20 pages.*
Cheung et al., "Whole genome amplification using a degenerate oligonucleotide primer allows hundreds of genotypes to be performed on less than one nanogram of genomic DNA", Proc Natl Acad Sci USA. 1996, vol. 93, 14676-14679.
Wang, Jing et al., "Study on the Factors Influencing the Whole Genome Amplification from a Single Cell by Degenerate Oligonucleotide Primered PCR", Journal of Anhui Agricultural Sciences 2008, vol. 36, No. 16, 6675-6677, Abstract Only.
Wan, Xiuqing et al., "Identification of Tobacco Transgenic Effects with Adaptor Ligation PCR Walking Methods", Tobacco Science & Technology 2007, No. 237, 49-53, Abstract Only.
International Search Report and Written Opinion for PCT/CN2012/083036, issued Jan. 17, 2013.

* cited by examiner

*Primary Examiner* — Angela M Bertagna
(74) *Attorney, Agent, or Firm* — Westman, Champlin & Koehler, P.A.; Z. Peter Sawicki; Amanda M. Prose (57) ABSTRACT

Provided are a method of constructing a nucleic acid library, a method of determining a nucleic acid sequence of a nucleic acid sample, and a kit thereof. The method of constructing the nucleic acid library includes the following steps: subjecting a nucleic acid sample to a DOP-PCR amplification, to obtain a first PCR amplification product; subjecting the first PCR amplification product to a second PCR amplification using a DOP-Amp primer, to obtain a second PCR amplification product; and subjecting the second PCR amplification product to an adaptor-ligation PCR, to obtain a third PCR amplification product, wherein the third PCR amplification product constitutes the nucleic acid library.

10 Claims, 5 Drawing Sheets

METHOD FOR PREPARING NUCLEIC ACID LIBRARY, ITS USES AND KITS

CROSS REFERENCE TO RELATED APPLICATIONS

This application is a Section 371 National Stage Application of International Application No. PCT/CN2012/083036, filed Oct. 16, 2012, and published as WO2013/056640 on Apr. 25, 2013, which claims priority and benefits of Chinese Patent Application No. 201110316066.8, filed with State Intellectual Property Office, P.R.C. on Oct. 18, 2011, the entire contents of which are incorporated herein by reference.

FIELD

Embodiments of the present disclosure generally relate to genetic engineering technology, more particularly, to a method of constructing a nucleic acid library and use thereof, and a kit.

BACKGROUND ART

The statements in this section merely provide background information related to the present disclosure and may not constitute prior art.

The Next-Generation sequencing (NGS) technology has changed the analytical model with DNA/RNA sample, becoming an essential tool in all of researching fields. The Next-Generation sequencing technology is that, by parallel sequencing millions of DNA short fragments simultaneously, it may complete sequencing each base during a short duration with sharply reduced cost. The Next-Generation sequencing technology has been applied to many aspects: such as genomics, transcriptomics, Epigenomics, and clinical diagnosis.

There are several kinds of the Next-Generation sequencing (NGS) platforms in current market, including Illumina Company's Genome Analyzer, Hiseq and Miseq series sequencing platform; Roche Company's 454 sequencing platform; Life Technologies Company's SOLID sequencing platform and Ion Torrent sequencing platform, etc.

However, regardless types of NGS platforms, DNA/RNA sample needs to be pre-treated prior to sequencing, to construct a DNA fragments library. Normally, the library construction needs an initial DNA/RNA amount of microgram level. Although the initial amount for library construction may be decreased after optimization, a nucleic acid sample of a single cell or in a trace amount still is still not able to be directly subjected to library construction, which has severely impeded the application of sequencing a single cell or a trace amount of nucleic acid sample.

Therefore, a library construction method for a single cell or a trace amount of nucleic acid sample needs to be developed in the art.

SUMMARY

Embodiments of the present disclosure seek to solve at least one of the problems existing in the prior art to at least some extent.

A purpose of the present disclosure is to provide a method of constructing a library with a single cell or a trace amount of nucleic acid sample, and use thereof.

Another purpose of the present disclosure is to provide a kit suitable for the above described method.

According to embodiments of a first broad aspect of the present disclosure, there is provided a method of constructing a nucleic acid library. According to embodiments of the present disclosure, the method may comprise following steps: subjecting a nucleic acid sample to a DOP-PCR amplification, to obtain a first PCR amplification product; subjecting the first PCR amplification product to a second PCR amplification using a DOP-Amp primer, to obtain a second PCR amplification product; subjecting the second PCR amplification product to an adaptor-ligation PCR, to obtain a third PCR amplification product, wherein the third PCR amplification product constitutes the nucleic acid library. According to embodiments of the present disclosure, the method may be used to effectively construct a nucleic acid library, particularly a nucleic acid library with a single cell or a trace amount of nucleic acid sample, and the obtained nucleic acid library may be effectively applied to a high-throughput sequencing platform, and may be used to effectively determine nucleotide sequence information of the nucleic acid sample. In addition, inventors of the present disclosure surprisingly found that the method of constructing a nucleic acid library of the present disclosure had a simple procedure, which can be easily manipulated, easily standardized, and easily promoted with characteristics of low cost, high sensitivity, high accuracy, and good repeatability.

According to embodiments of a second broad aspect of the present disclosure, there is provided a method of determine a nucleotide sequence of a nucleic acid sample. According to embodiments of the present disclosure, the method may comprise: constructing a nucleic acid library with the nucleic acid sample using the method according to the method of constructing the nucleic acid library in the embodiments of the present disclosure; and subjecting the nucleic acid library to sequencing and data analysis, to determine the nucleotide sequence of the nucleic acid sample. The inventors of the present disclosure found that, the method may be used to effectively determine nucleotide sequence information of the nucleic acid sample, particularly the nucleotide sequence information of a single cell or a trace amount of the nucleic acid sample, which has a simple procedure with characteristics of low cost, high sensitivity, high accuracy, and good repeatability.

According to embodiments of a third aspect of the present disclosure, there is provided a kit. According to embodiments of the present disclosure, the kit may comprise: a DOP primer; a DOP-Amp primer; and an adaptor-ligation primer. According to embodiments of the present disclosure, the kit is used for the above described method of constructing a nucleic acid library and the method of determining a nucleotide sequence of a nucleic acid sample. The inventors of the present disclosure found that, the kit of the present disclosure may be used combining with the above described method of constructing a nucleic acid library or the method of determining a nucleotide sequence of a nucleic acid sample, to effectively construct the nucleic acid library with the nucleic acid sample, particularly with a single cell or a trace amount of the nucleic acid sample, and the obtained nucleic acid library may be effectively applied to a high-throughput sequencing platform, and may be used to effectively determine nucleotide sequence information of the nucleic acid sample, by which the obtained nucleotide sequence information has a high sensitivity and a good repeatability.

In details, according to embodiments of the present disclosure, the method of constructing a nucleic acid library, the method of determining a nucleotide sequence of a nucleic acid sample, and the kit also have following features:

In a first aspect of the present disclosure, there is provided a method of constructing a nucleic acid library. According to embodiments of the present disclosure, the method comprises following steps of:

a). providing a sample to be tested, the sample comprises a nucleic acid having a total content of 2 pg to 1 µg;

b). subjecting the sample to be tested to a DOP-PCR amplification, to obtain a first PCR amplification product;

c). subjecting the first PCR amplification product to a second PCR amplification using a DOP-Amp primer, to obtain a second PCR amplification product;

d). subjecting the second PCR amplification product to an adaptor-ligation PCR, to obtain a third PCR amplification product, wherein the third PCR amplification product constitutes the nucleic acid library.

According to embodiments of the present disclosure, the third PCR amplification product has adaptors at both 5'-end and 3'-end.

According to embodiments of the present disclosure, the method further comprises a step e): subjecting the third PCR amplification product to a fragment selection, to obtain selected fragments.

According to embodiments of the present disclosure, the sample in step a) is selected from following groups:
a sample composed of 1 to 200 single cells, or
a nucleic acid sample comprising 1 to 200 single cells, or
a nucleic acid sample has a nucleic acid in a total content of 2 pg to 1 µg.

According to embodiments of the present disclosure, the sample is selected from following groups:
a trace amount of genome DNA, immune-precipitation product DNA, plasma DNA, cDNA, or a combination thereof.

According to embodiments of the present disclosure, the DNA derives from environment, preferably, derives from soil and/or water.

According to embodiments of the present disclosure, the DNA derives from body fluid or excreta, preferably, derives from plasma and/or urine.

According to embodiments of the present disclosure, the DNA is subjected to a chemical treatment or a physical treatment, preferably, the DNA is subjected to a bisulfate treatment.

According to embodiments of the present disclosure, a DOP primer having a degenerate oligonucleotide region is used in step b) for randomly amplifying DNA sample.

According to embodiments of the present disclosure, the DOP primer comprises a non-degenerate oligonucleotide region located at 5'-end of the DOP primer, the degenerate oligonucleotide region located in the middle of the DOP primer, and an anchor region located at 3'-end of the DOP primer; or the DOP primer comprises a non-degenerate oligonucleotide region located at 5'-end of the DOP primer, and the degenerate oligonucleotide region located in the middle of the DOP primer and at 3'-end of the DOP primer. According to embodiments of the present disclosure, the anchor region located at 3'-end of the DOP primer has a length of 2 to 12 nucleotides, preferably, 4 to 8 nucleotides.

According to embodiments of the present disclosure, the anchor region located at 3'-end of the DOP primer has a nucleotide sequence of at least one selected from TG, ATGTGG, TGTGG and GTCT.

According to embodiments of the present disclosure, the non-degenerate oligonucleotide region located at 5'-end of the DOP primer has a nucleotide sequence shown as SEQ ID NO: 2; or has a nucleotide sequence with at least 50% homology to SEQ ID NO: 2.

According to embodiments of the present disclosure, the non-degenerate oligonucleotide region located at 5'-end of the DOP primer has a length of 5 to 30 nt, preferably 5 to 20 nt, more preferably 6 to 13 nt.

According to embodiments of the present disclosure, a sequence of the degenerate oligonucleotide region is shown as (N)m, in which N in a position of each base comprises A, T, G and C, m is a positive integer of 3 to 20.

According to embodiments of the present disclosure, the DOP-Amp primer in step c) is complementary or substantially complementary to the non-degenerate oligonucleotide region located at 5'-end of the DOP primer in step b).

According to embodiments of the present disclosure, the DOP-Amp primer binds to the non-degenerate oligonucleotide region located at 5'-end of the DOP primer.

According to embodiments of the present disclosure, the DOP-Amp primer has a nucleotide sequence shown as SEQ ID NO: 2.

According to embodiments of the present disclosure, the second PCR amplification product is subjected to the adaptor-ligation PCR using an adaptor-ligation primer in step d).

According to embodiments of the present disclosure, the adaptor primers are P5 and P7 both, respectively having a non-degenerate oligonucleotide region located at 3'-end of P5 or P7, which can bind to a sequence of the DOP-Amp primer, the non-degenerate oligonucleotide region has a nucleotide sequence being same or fully complementary to SEQ ID NO: 2, or has a nucleotide sequence with at least 80% homology to SEQ ID NO: 2.

According to embodiments of the present disclosure, the adaptor primer P7 further has an index (or barcode) sequence.

According to embodiments of the present disclosure, the selected fragments in step e) have a length of 100 to 1000 bp.

According to embodiments of the present disclosure, the selected fragments have a length of 200 to 500 bp.

In a second aspect of the present disclosure, there is provided a method of determining a nucleotide sequence of a nucleic acid sample. According to embodiments of the present disclosure, the method comprises following steps of:

(i) constructing a nucleic acid library of the sample with a single cell or a trace amount of nucleic acid sample using any one of the methods described in the first aspect of the present disclosure;

subjecting the nucleic acid library to sequencing and data analysis

According to embodiments of the present disclosure, the nucleic acid library is subjected to sequencing by a Next-Generation high-throughput sequencing platform, the Next-Generation high-throughput sequencing platform may be at least one selected from a group consisting of Roche454 FLX, Illumina Solexa, ABI SOLID.

According to embodiments of the present disclosure, the step of sequencing comprises:
subjecting the nucleic acid library to hybridization with a sequencing probe fixed on a flow cell, and to a bridge solid phase PCR amplification, to obtain a sequencing cluster;
subjecting the sequencing cluster to sequencing by means of sequencing by synthesis method, to obtain nucleotide sequence information in the sample.

In a third aspect of the present disclosure, there is provided a kit which may be used in any one of the methods in the first aspect and the second aspect of the present disclosure. According to embodiments of the present disclosure, the kit comprises:

(1) a DOP primer for a first PCR amplification provided in a first container;

(2) a DOP-Amp primer for a second PCR amplification provided in a second container;

(3) an adaptor-ligation primer for a third PCR amplification provided in a third container;

(4) a specification.

According to embodiments of the present disclosure, the kit further comprises: a reagent required for PCR amplification, a reagent for nucleic acid purification, a flow cell for high-throughput sequencing, or a combination thereof.

Additional aspects and advantages of the present disclosure will be given in part in the following descriptions, become apparent in part from the following descriptions, or be learned from the practice of the present disclosure.

BRIEF DESCRIPTION OF THE DRAWINGS

These and other aspects and advantages of embodiments of the present disclosure will become apparent and more readily appreciated from the following descriptions made with reference the accompanying drawings, in which:

FIG. 4 shows a fragment detection result of adaptor-ligation PCR products respectively deriving from 4 samples (YH1, YH2, YH3, T21) after fragment selection and purification, when constructing a nucleic acid library by the method of constructing a nucleic acid library of the present disclosure, according to an embodiment of the present disclosure, in which FIG. 4A shows a fragment detection result of YH1 sample with a desired major band located at 377 bp; FIG. 4B shows a fragment detection result of YH2 sample with a desired major band located at 326 bp; FIG. 4C shows a fragment detection result of YH3 sample with a desired major band located at 339 bp; and FIG. 4D shows a fragment detection result of T21 sample with a desired major band located at 360 bp;

FIG. 6 shows a fragment detection result of nucleic acid libraries after fragment selection and purification, when constructing a nucleic acid library with a trace amount of DNA/cDNA sample by the method of constructing a nucleic acid library of the present disclosure, according to an embodiment of the present disclosure, in which, FIG. 6A shows a fragment detection result with a trace amount 200 pg of genome DNA, FIG. 6B shows a fragment detection result with a trace amount 40 pg of genome DNA, FIG. 6C shows a fragment detection result with 200 pg of IP product DNA, FIG. 6D shows a fragment detection result with 40 pg of IP product DNA, FIG. 6E shows a fragment detection result of cDNA with the original concentration (abbreviating as O.C.), FIG. 6F shows a fragment detection result of cDNA-$5^{-1}$, FIG. 6G shows a fragment detection result of 200 pg of plasma DNA.

DETAILED DESCRIPTION

Reference will be made in detail to embodiments of the present disclosure. The same or similar elements and the elements having same or similar functions are denoted by like reference numerals throughout the descriptions. The embodiments described herein with reference to drawings are explanatory, illustrative, and used to generally understand the present disclosure. The embodiments shall not be construed to limit the present disclosure.

In addition, terms such as "first", "second" and "third" are used herein for purposes of description and are not intended to indicate or imply relative importance or significance. Therefore, features restricted with "first", "second" may explicitly or implicitly comprise one or more of the features. Furthermore, in the description of the present disclosure, unless otherwise stated, the term "a plurality of" refers to two or more.

A purpose of the present disclosure is to provide a method of constructing a library with a single cell or a trace amount of nucleic acid sample, and use thereof.

Another purpose of the present disclosure is to provide a kit suitable for the above described method.

Method of Constructing a Nucleic Acid Library

Figure 2:
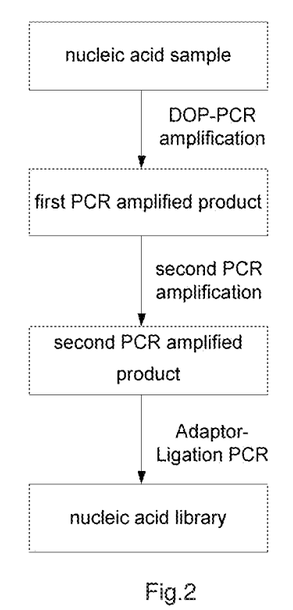
FIG. 2 is a flow chart showing a method of constructing a nucleic acid library according to an embodiment of the present disclosure.

According to embodiments of one aspect of the present disclosure, there is provided a method of constructing a nucleic acid library. According to embodiments of the present disclosure, referring to FIG. 2, in the method:

A nucleic acid sample is subjected to a DOP-PCR amplification, to obtain a first PCR amplification product. According to embodiments of the present disclosure, the method of constructing the nucleic acid library of the present disclosure is particularly suitable for a single cell or a trace amount of nucleic acid sample, in which, a content of the nucleic acid is not subjected to special restrictions. According to specific examples of the present disclosure, the nucleic acid sample has a content of 2 pg to 1 µg. According to embodiments of the present disclosure, a source of the nucleic acid is also not subjected to special restrictions. According to some embodiments of the present disclosure, the nucleic acid sample may derive from 1 to 200 single cells. According to some specific examples of the present disclosure, the nucleic acid sample may be at least one selected from a trace amount of genome DNA, immune-precipitation product NDA, plasma DNA and cDNA. According to some embodiments of the present disclosure, the nucleic acid sample may derive from at least one selected from a group consisting of environment, body fluid and excreta. According to some specific examples of the present disclosure, the nucleic acid sample may derive from at least one selected from soil and water. According to other specific examples of the present disclosure, the nucleic acid sample derives from at least one selected from plasma and urine.

According to embodiments of the present disclosure, prior to the step of subjecting the nucleic acid sample to the DOP-PCR amplification, the method further comprises a step of subjecting the nucleic acid sample to a treatment, for example, when the nucleic acid sample is a single cell, it may be subjected to a treatment of lysing cell, to release genomic DNA, which may improve the efficiency of the DOP-PCR amplification with the nucleic acid sample, so as to benefit to subsequent steps. According to a specific example, when the nucleic acid is a single cell, prior to the step of subjecting the nucleic acid sample to the DOP-PCR amplification, the method further comprises a step of subjecting to a treatment of lysing the single cell by means of an alkaline lysis buffer.

According to some embodiments of the present disclosure, prior to the step of subjecting the nucleic acid sample to the DOP-PCR amplification, the method further comprises a step of subjecting the nucleic acid sample to a chemical treatment or a physical treatment. According to some specific examples of the present disclosure, the above described chemical treatment is a bisulfate treatment. Thus, the nucleic acid sample may be suitable for constructing a nucleic acid library.

According to embodiments of the present disclosure, a reaction condition for the DOP-PCR amplification is not subjected to special restrictions. According to some embodiments of the present disclosure, the nucleic acid sample is subjected to the DOP-PCR amplification using a DOP primer, in which the DOP primer has a degenerate oligonucleotide region; and the DOP primer comprises a non-degenerate oligonucleotide region located at 5'-end of the DOP primer, the degenerate oligonucleotide region located in the middle of the DOP primer, and an anchor region located at 3'-end of the DOP primer. According to other embodiments of the present disclosure, the DOP primer comprises: a non-degenerate oligonucleotide region located at 5'-end of the DOP primer; and the degenerate oligonucleotide region located in the middle of the DOP primer and at 3'-end of the DOP primer. Specific structures of the anchor region located at 3'-end of the DOP primer, the non-degenerate oligonucleotide region located at 5'-end of the DOP primer, and the degenerate oligonucleotide region of the DOP primer are not subjected to special restrictions. According to embodiments of the present disclosure, the anchor region located at 3'-end of the DOP primer has a length of 2 to 12 nucleotides. According to other embodiments of the present disclosure, the anchor region located at 3'-end of the DOP primer has a length of 4 to 8 nucleotides. According to embodiments of the present disclosure, the anchor region located at 3'-end of the DOP primer has a nucleotide sequence of at least one selected from TG, ATGTGG, TGTGG and GTCT. According to some embodiments of the present disclosure, the non-degenerate oligonucleotide region located at 5'-end of the DOP primer has a nucleotide sequence shown as SEQ ID NO: 2. According to other embodiments of the present disclosure, the non-degenerate oligonucleotide region located at 5'-end of the DOP primer has a nucleotide sequence with at least 50% homology to SEQ ID NO: 2. According to embodiments of the present disclosure, the non-degenerate oligonucleotide region located at 5'-end of the DOP primer has a length of 5 to 30 nt, preferably 5 to 20 nt, more preferably 6 to 13 nt. According to embodiments of the present disclosure, the degenerate oligonucleotide region has a length of 3 to 20 nucleotides. Thus, efficiency of the DOP-PCR amplification may be effectively improved, so as to effectively improve the efficiency of constructing a nucleic acid library.

Then, the first PCR amplification product is subjected to a second PCR amplification using a DOP-Amp primer, to obtain a second PCR amplification product. According to embodiments of the present disclosure, a specific structure of the DOP-Amp primer is not subjected to special restrictions. According to some specific examples of the present disclosure, the DOP-Amp primer is complementary or substantially complementary to the non-degenerate oligonucleotide region located at 5'-end of the DOP primer. Thus, the first PCR amplification product may be effectively subjected to the second PCR amplification. According to other embodiments of the present disclosure, the DOP-Amp primer may bind to the non-degenerate oligonucleotide region located at 5'-end of the DOP primer. According to some specific examples of the present disclosure, the DOP-Amp primer has a nucleotide sequence shown as SEQ ID NO: 2. Thus, the efficiency of the second PCR amplification may be effectively improved.

Then, the second PCR amplification product is subjected to an adaptor-ligation PCR, to obtain a third PCR amplification product, such third PCR amplification product constitutes the desired nucleic acid library. According to embodiments of the present disclosure, a reaction condition for the adaptor-ligation PCR is not subjected to special restrictions. According to some embodiments of the present disclosure, the second PCR amplification product is subjected to the adaptor-ligation PCR using an adaptor-ligation primer, in which the adaptor-ligation primer has a nucleotide sequence matching with the DOP-Amp primer at 3'-end. According to other embodiments of the present disclosure, the adaptor-ligation primer comprises an index sequence. Therefore, a nucleic acid library comprising the index sequence may be effectively constructed. And then, when constructing the nucleic acid libraries with a plurality of the nucleic acid samples by the method of constructing the nucleic acid library of the present disclosure, with mutually different index sequences of each libraries, the nucleic acid libraries of the plurality of the nucleic acid samples may be simultaneously subjected to a high-throughput sequencing, so as to effectively improve the sequencing efficiency with low cost under the premise of ensuring accuracy and repeatability.

According to embodiments of the present disclosure, the obtained third PCR amplification product has adaptors both at 5'-end and 3'-end.

According to embodiments of the present disclosure, the method of constructing a nucleic acid library of the present disclosure may further comprise: the third PCR amplification product is subjected to a fragment selection. Accordingly, the third PCR amplification product may be selected in accordance with the fragment size, to remove interference. According to embodiments of the present disclosure, specific reaction conditions for the fragment selection is not subjected to special restrictions, which may be selected according to specific experimental conditions, to obtain the third PCR amplification product having an appropriate length, for example, when the constructed nucleic acid library is subjected to sequencing on a platform of Illumina Hiseq2000, the selected fragments from the third PCR amplification product may have a length of 200 to 800 bp. According to specific examples of the present disclosure, the selected fragments from the third PCR amplification product may have a length of 100 to 1000 bp. According to other embodiments of the present disclosure, the selected fragments from the third PCR amplification product may have a length of 200 to 500 bp.

According to embodiments of the present disclosure, such method may be used to effectively construct the nucleic acid sample, particularly the nucleic acid library with a single cell or a trace amount of nucleic acid sample; and the obtained nucleic acid library may be effectively applied on a high-throughput sequencing platform, which may further effectively determine the nucleotide sequence information of the nucleic acid sample. In addition, inventors surprisingly found that, the method of constructing the nucleic acid library of the present disclosure had a simple procedure, which can be easily manipulated, easily standardized, and easily promoted with characteristics of low cost, high sensitivity, high accuracy, and good repeatability.

In addition, it should note that whether the second PCR amplification product is subjected to the adaptor-ligation PCR may be selected in accordance with the use of the nucleic acid library. In details, when the constructed nucleic acid library is subjected to sequencing by Sanger method, the second PCR amplification product may be not subjected to the adaptor-ligation PCR, but directly subjected to electrophoresis or concentration assay and subsequent Sanger sequencing method; or may be subjected to Sanger sequencing method after being prepared as a plasmid. While, when the constructed nucleic acid library is subjected to high-throughput sequencing, such as Illumina sequencing, the second PCR amplification product may be subjected to the adaptor-ligation PCR, to obtain a nucleic acid library with sequencing adaptor, for conveniently performing subsequent sequencing.

Method of Determining a Nucleotide Sequence of a Nucleic Acid Sample

Figure 1:
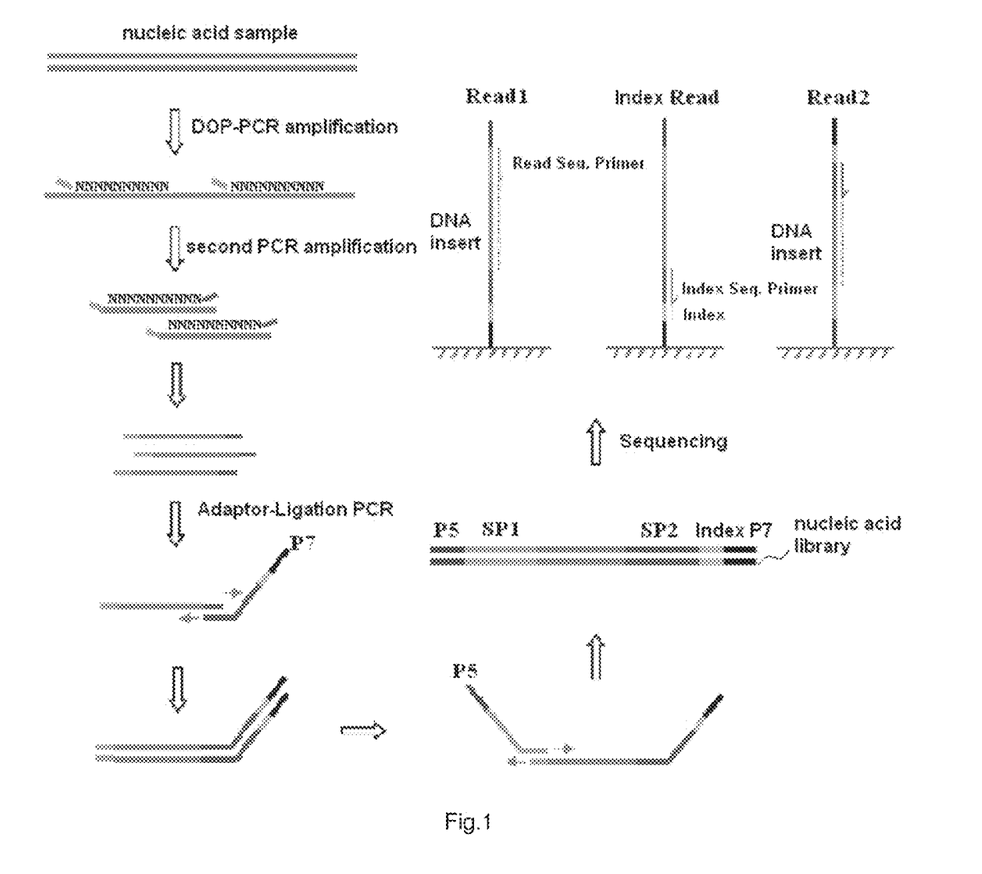
FIG. 1 is a flow chart showing a method of determining a nucleotide sequence of a nucleic acid sample according to an embodiment of the present disclosure.

According to another aspect of the present disclosure, there is provided a method of determining a nucleotide sequence of a nucleic acid sample. According to embodiments of the present disclosure, referring to FIG. 1 and FIG. 2, in this method:

(i) a nucleic acid library of a nucleic acid sample is constructed by the method of constructing a nucleic acid library according to embodiments of the present disclosure. According to embodiments of the present disclosure, types of the nucleic acid sample is not subjected to special restrictions, which may be an untreated single cell, or may be a trace amount of nucleic acid such as DNA or cDNA. According to embodiments of the present disclosure, the nucleic acid sample may be at least one selected from a single cell or a trace amount of nucleic acid sample.

(ii) the nucleic acid library is subjected to sequencing and data analysis, to determine the nucleotide sequence of the nucleic acid sample. According to embodiments of the present disclosure, methods and apparatuses for performing sequencing are not subjected to special restrictions. According to some embodiments of the present disclosure, the nucleic acid library is subjected to sequencing by a high-throughput sequencing platform. According to some specific examples, the nucleic acid library is subjected to sequencing by at least one selected from a group consisting of Roche454 FLX, Illumina Solexa, ABI SOLID. Then, the sequencing efficiency may be improved, to effectively determine the nucleotide sequence of the nucleic acid sample.

The inventors found that, such method may be used in effectively determining the nucleotide sequence information of the nucleic acid sample, particularly of a single cell or a trace amount of nucleic acid sample, which has a simple procedure with characteristics of low cost, high sensitivity, high accuracy, and good repeatability.

According to a still another aspect of the present disclosure, there is provided a kit. According to embodiments of the present disclosure, the kit comprises: a DOP primer; a DOP-Amp primer; and an adaptor-ligation primer.

According to embodiments of the present disclosure, in the kit of the present disclosure, the DOP primer, the DOP-Amp primer and the adaptor-ligation primer are placed respectively in different containers.

According to embodiments of the present disclosure, in the kit of the present disclosure, sequence and structure of the DOP primer are not subjected to special restrictions. According to some embodiments of the present disclosure, the DOP primer has a degenerate oligonucleotide region, in which the DOP primer comprises: a non-degenerate oligonucleotide region located at 5'-end of the DOP primer; the degenerate oligonucleotide region located in the middle of the DOP primer; and an anchor region located at 3'-end of the DOP primer. According to other embodiments of the present disclosure, the DOP primer comprises: a non-degenerate oligonucleotide region located at 5'-end of the DOP primer; the degenerate oligonucleotide region located in the middle of the DOP primer and at 3'-end of the DOP primer. According to embodiments of the present disclosure, specific structures of the anchor region located at 3'-end of the DOP primer, the non-degenerate oligonucleotide region located at 5'-end of the DOP primer, and the degenerate oligonucleotide region of the DOP primer are not subjected to special restrictions. According to some embodiments of the present disclosure, the anchor region located at 3'-end of the DOP primer has a length of 2 to 12 nucleotides. According to other embodiments of the present disclosure, the anchor region located at 3'-end of the DOP primer has a length of 4 to 8 nucleotides. According to some embodiments of the present disclosure, the anchor region located at 3'-end of the DOP primer has a nucleotide sequence of at least one selected from TG, ATGTGG, TGTGG and GTCT. According to some specific examples of the present disclosure, the non-degenerate oligonucleotide region located at 5'-end of the DOP primer has a nucleotide sequence shown as SEQ ID NO: 2. According to some embodiments of the present disclosure, the non-degenerate oligonucleotide region located at 5'-end of the DOP primer has a nucleotide sequence with at least 50% homology to SEQ ID NO: 2. According to some embodiments of the present disclosure, the non-degenerate oligonucleotide region located at 5'-end of the DOP primer has a length of 5 to 30 nt, preferably 5 to 20 nt, more preferably 6 to 13 nt. According to other embodiments of the present disclosure, the degenerate oligonucleotide region has a length of 3 to 20 nucleotides. Accordingly, when constructing a nucleic acid library with a single cell or a trace amount of nucleic acid sample by the kit of the present disclosure, the efficiency of the DOP-PCR amplification may be effectively improved, so as to effectively improve the efficiency of constructing the nucleic acid library.

According to embodiments of the present disclosure, in the kit of the present disclosure, specific structure of the DOP-Amp primer is not subjected to special restrictions. According to some specific examples of the present disclosure, the DOP-Amp primer is complementary or substantially complementary to the non-degenerate oligonucleotide region located at 5'-end of the DOP primer. Accordingly, when constructing a nucleic acid library with a single cell or a trace amount of nucleic acid sample by the kit of the present disclosure, the first PCR amplification product may be effectively subjected to the second PCR amplification, so as to effectively construct the nucleic acid library. According to other embodiments of the present disclosure, the DOP-Amp primer may bind to the non-degenerate oligonucleotide region located at 5'-end of the DOP primer. According to some specific examples of the present disclosure, the DOP-Amp primer has a nucleotide sequence shown as SEQ ID NO: 2. Accordingly, when constructing a nucleic acid library with a single cell or a trace amount of nucleic acid sample by the kit of the present disclosure, the efficiency of the second PCR amplification may be effectively improved, so as to effectively improve the efficiency of constructing the nucleic acid library.

According to embodiments of the present disclosure, in the kit of the present disclosure, specific structure of the adaptor-ligation primer are not subjected to special restrictions. According to some specific examples of the present disclosure, the adaptor-ligation primer has a nucleotide sequence matching with the DOP-Amp primer at 3'-end. According to other embodiments of the present disclosure, the adaptor-ligation primer comprises an index sequence. Accordingly, the kit of the present disclosure may be used to effectively construct the nucleic acid library comprising the index sequence. And then, when constructing the nucleic acid libraries with a plurality of the nucleic acid samples by the kit of the present disclosure, with mutually different index sequences of each libraries, the nucleic acid libraries of the plurality of the nucleic acid samples may be simultaneously subjected to a high-throughput sequencing, so as to effectively improve the sequencing efficiency with low cost under the premise of ensuring accuracy and repeatability.

According to embodiments of the present disclosure, the kit is suitable for the above described methods of constructing a nucleic acid library and determining a nucleotide sequence of a nucleic acid sample. The inventors found that, by means of the kit of the present disclosure, combing with the above described methods of constructing a nucleic acid library and determining a nucleotide sequence of a nucleic acid sample, a nucleic acid library may be effectively constructed with the nucleic acid sample, particularly a single cell or a trace amount of nucleic acid library, and the obtained nucleic acid library may be effectively applied on a high-throughput sequencing platform, which may effective determine the nucleotide sequence information of the nucleic acid sample, with high accuracy and good repeatability.

It should note that, the above described method of constructing a nucleic acid library with a single cell or a trace amount of nucleic acid sample is the first to be built through extensive and in-depth studies by the inventors of the present disclosure. Using the method of the present disclosure, a nucleic acid library may be constructed and then subjected to sequencing for body fluid of a patient, which may effectively obtain disease-related gene information of the patient from the sample, so as to provide important information for preventing and treating human diseases.

In addition, specific meanings of terms and expressions used herein are shown below:

The term "comprise" used herein may represent meanings of "include", "substantially be composed of" and "be composed of".

The terms "at least" and "no more than" used herein include the mentioned number itself, for example "at least 80%" means ≥80%, "no more than 2%" means ≤2%.

Primer

The term "primer" used herein is a genetic term of oligonucleotide which is complementary and paired to a template, and may synthesize DNA strand complementary with the template under an effect of DNA polymerase. The primer may be natural RNA, DNA, or may be natural nucleotide in any forms, or even may be non-natural nucleotides such as LNA or ZNA, etc.

DOP-PCR (Degenerate Oligonucleotide Primed PCR)

DOP-PCR, i.e. degenerate oligonucleotide primer PCR, is an amplification method for a trace amount DNA or a single cell, includes (but not limited to): two steps of a low stringency amplification and a high stringency amplification. The low stringency amplification is based on a DOP primer, directing at adding a fixed sequence as a PCR primer binding region in the DNA fragment; then the amplification product obtained by low stringency amplification is subjected to the high stringency amplification using a DOP-Amp primer.

DOP primer, i.e. degenerate oligonucleotide primer which comprises at least two parts, from 5'-end to 3'-end respectively are: a non-degenerate oligonucleotide region located at 5'-end of the DOP primer and a degenerate oligonucleotide region downstream thereof. According to embodiments of the present disclosure, the DOP primer has a sequence shown as SEQ ID NO: 1 (GCTCTTCCGATCTNNNNNNNNNN), in which GCTCTTCCGATCT (SEQ ID NO: 2) is the region without degenerate oligonucleotides at 5'-end, NNNNNNNNNN is the degenerate oligonucleotide region, the sequence of the degenerate oligonucleotides may be recorded as (N)m, m is a positive integer selected from 3 to 20, N is independently selected from A, T, G and C. According to embodiments of the present disclosure, the DOP primer may also comprise an anchor region located at 3'-end of the DOP primer, such as "TG", "ATGTGG", "GTCT", etc. Using the DOP primer for PCR amplification, the DOP primer may be subjected to randomly binding to the nucleic acid sample by means of base complementary pairing, to amplify the randomly fragmented sample. In the method of constructing a nucleic acid library of the present disclosure, the DOP primer is used in DOP-PCR amplification with the nucleic acid sample, to obtain the first PCR amplification product.

DOP-Amp primer is substantially complementary with a specific nucleotide sequence of the DOP primer, which may be used in further amplifying the first PCR amplification product by the DOP primer. According to embodiments of the present disclosure, the sequence of the DOP-Amp primer is complementary or substantially complementary with the non-degenerate oligonucleotide region located at 5'-end of the above described DOP primer. According to an embodiment of the present disclosure, the DOP-Amp primer is same as the non-degenerate oligonucleotide region located at 5'-end of the DOP primer, or at least covers 50% of the non-degenerate oligonucleotide region located at 5'-end of the DOP primer, or has nucleotide sequence with at least 50% homology to SEQ ID NO: 2. According to another embodiment of the present disclosure, the DOP-Amp primer has a nucleotide sequence shown as SEQ ID NO: 2 (5'-GCTCTTC-CGATCT-3'). In the method of constructing a nucleic acid library of the present disclosure, the DOP-Amp primer is used in subjecting the first PCR amplification product to a second PCR amplification, to obtain a second PCR amplification product.

Adaptor-Ligation PCR

Adaptor-Ligation PCR refers to ligating adaptors at both two ends of a template DNA while performing PCR, in which the "adaptor" used herein, is an adaptor sequence of the library for the high-throughput sequencing, and the adaptor-ligation primer is an important component of the adaptor-ligation PCR.

According to an embodiment of the present disclosure, the above described adaptor-ligation primer includes (but not limited to): P5 and P7, in which P5 has a nucleotide sequence shown as SEQ ID NO: 3 (AATGATACGGCGACCAC-CGAGATCTACACTCTTTCCCTACAC-GACGCTCTTCCGATCT); P7 has any one of the nucleotide sequences shown as SEQ ID NO: 4-7, which may be represented as CAAGCAGAAGACGGCATAC-GAGATXXXXXXGTGACTGGAGTTCA-GACGTGTGCTCTT CCGATCT, in which XXXXXX is an index sequence, for distinguishing different nucleic acid samples.

In addition, it should note that, the method of constructing a nucleic acid library and the method of determining a nucleotide sequence of a nucleic acid sample of the present disclosure at least have following advantages:

1. The method of constructing a nucleic acid library of the present disclosure, by subjecting DNA of a nucleic acid sample to a DOP-PCR amplification using a DOP primer, may completely cover the DNA fragments of the nucleic acid sample;

2. In the method of constructing a nucleic acid library of the present disclosure, the DOP primer at least has a non-degenerate nucleotide region located at 5'-end of the DOP primer and a degenerate nucleotide region downstream thereof, and the obtained first PCR amplification product has a specific nucleotide sequence, after adding the DOP-Amp primer, the first PCR amplification product may be subjected to a second amplifying, to obtain a second PCR amplification product, and the second PCR amplification is a high stringency amplification, which may greatly improve the sensitivity of amplification;

3. In the method of constructing a nucleic acid library of the present disclosure, the adaptor-ligation PCR uses an adaptor-ligation primer to ligate adaptors at both ends of the second PCR amplification product, to obtain a third PCR amplification product, which may be directly used for subsequent step of sequencing;

4. The method of constructing a nucleic acid library and the method of determining a nucleotide sequence of a nucleic acid sample of the present disclosure may be used in subjecting a plurality of nucleic acid samples to library construction and sequencing simultaneously, without an interference of fluorescence background;

5. The method of constructing a nucleic acid library and the method of determining a nucleotide sequence of a nucleic acid sample of the present disclosure are not subjected to special restrictions, all of human, animals, microorganism, plants and etc., may be used in the method of constructing a nucleic acid library and the method of determining a nucleotide sequence of a nucleic acid sample of the present disclosure, for performing library constructing and sequencing individually;

6. The method of constructing a nucleic acid library and the method of determining a nucleotide sequence of a nucleic acid sample of the present disclosure have a low cost of experiment, a high sensitivity, a high accuracy, and a good repeatability.

Reference will be made in detail to examples of the present disclosure. It would be appreciated by those skilled in the art that the following examples are explanatory, and cannot be construed to limit the scope of the present disclosure. If the specific technology or conditions are not specified in the examples, a step will be performed in accordance with the techniques or conditions described in the literature in the art (for example, referring to J. Sambrook, et al. (translated by Huang P T), *Molecular Cloning*: A Laboratory Manual, 3rd Ed., Science Press) or in accordance with the product instructions. If the manufacturers of reagents or instruments are not specified, the reagents or instruments may be commercially available, for example, from Illumina Company.

Example 1

Constructing and Sequencing of a Single Cell Genome DNA Library

The present example was carried out on a single cell derives from lymphocytes in human blood, by the method of constructing a nucleic acid library of the present disclosure, a single cell genome DNA library of each sample was constructed respectively, specific steps were shown as below:

1. Sample Source

The blood single cell sample derived from peripheral blood of a normal human (YH, YanHuang project sample) or a patient with Down's syndrome (T21).

2. Single Cell Isolation 3 of YH samples (YH1, YH2 and YH3) and 1 of T21 sample deriving single lymphocytic cell of peripheral blood were isolated by mouth-controlled pipette, and placed respectively in PCR tubes containing 2 μL of an alkaline lysis buffer (200 mM KOH, 50 mM DTT), then subsequently frozen at −80° C. for at least 30 minutes for use.

3. DOP-PCR amplifying (i.e. low stringency amplification, pre-amplification):

Each of the above described PCR tubes was respectively subjected to a treatment at 65° C. for 15 minutes, to respectively obtain 4 samples of single cell DNA; and then a DOP reaction system of each sample of the single cell DNA was respectively prepared in accordance with the ratio shown in Table 1.

TABLE 1

| Component | Final Concentration |
|---|---|
| 10 x Pfx amplification buffer | 1 x |
| 10 x Enhancer Solution | 1 x |
| 10 mM dNTP mixed buffer | 1 mM of each |
| 50 mM MgSO$_4$ | 1 mM |
| DOP primer | 0.3~2 μM |
| pfx DNA polymerase | 1~2.5 units |
| single cell DNA | as required |
| sterilized distilled water | up to desired volume |

When comparing the DOP reaction system, each of the above described components in Table 1 would be mixed and covered with an appropriate mineral oil; and after covered with a cap thereof, the PCR tubes were subjected to an instant centrifuging. Besides, in each of the DOP reaction system, the DOP primer had a sequence of GCTCTTCCGATCT-NNNNNNNNNN (SEQ ID NO: 1), in which the non-degenerate oligonucleotide region located at 5'-end had a sequence of GCTCTTCCGATCT (SEQ ID NO: 2), the degenerate nucleotides region had a sequence of NNNNNNNNNN, in which N could be any one of A, T, G and C.

Then, in accordance with the reaction conditions shown in Table 2, each of the DOP reaction systems obtained by the above described preparation was subjected to a DOP-PCR amplification, to obtain a first PCR amplification product.

TABLE 2

| Temperature | Duration | Cycles |
|---|---|---|
| 94~98° C. | 2~5 minutes | 1 |
| 94~98° C. | 20 seconds~2 minutes | 1~10 |
| 10~19° C. | 5~30 minutes | |
| 20~30° C. | 5~30 minutes | |
| 31~40° C. | 5~30 minutes | |
| 65~72° C. | 15 seconds~3 minutes | |
| 4~12° C. | hold | |

Since the DOP primer comprised a non-degenerate oligonucleotide region located at 5'-end of the DOP primer and a degenerate oligonucleotide region located at 3'-end of the DOP primer, the DOP-PCR amplification could add non-degenerate oligonucleotide regions located at 5'-end of the DOP primer to both ends of the first PCR amplification product.

4. Second Amplification (i.e. High Stringency Amplification)

The DOP-Amp primer, which could bind to the above described non-degenerate oligonucleotide region located at 5'-end of the DOP primer, was respectively added into each of the DOP reaction systems obtained from the DOP-PCR amplification, to reach a final concentration of 2 μM, so as to respectively obtain each second PCR amplification reaction system. The DOP-Amp primer had a sequence of GCTCT-TCCGATCT (SEQ ID NO: 2), i.e. the DOP-Amp primer comprise a part of the non-degenerate oligonucleotide region located at 5'-end of the above described DOP primer.

Then, in accordance with the reaction conditions shown in Table 3, each of the second PCR amplification reaction system was subjected to a second amplification, to obtain a second PCR amplification product.

TABLE 3

| Temperature | Duration | Cycles |
| --- | --- | --- |
| 94~98° C. | 2~5 minutes | 1 |
| 94~98° C. | 15 seconds~2 minutes | 5~30 |
| 50~60° C. | 15 seconds~2 minutes | |
| 65~72° C. | 15 seconds~2 minutes | |
| 4~12° C. | hold | |

Then, the above obtained second PCR amplification products were subjected to electrophoresis and concentration assay, the qualified products were preserved for use.

5. Adaptor-Ligation PCR

In accordance with the ratio shown in Table 4, an adaptor-ligation PCR reaction system of each second PCR amplification product obtained in step 4 was prepared respectively. The used DNA polymerase is a thermo-tolerant DNA polymerase pfx enzyme.

TABLE 4

| Components | Final Concentration |
| --- | --- |
| 10 x Pfx Amplification Buffer | 2 x |
| 10 x Enhancer Solution | 1x |
| 10 mM dNTP mixed buffer | 01 mM of each |
| 50 mM MgSO4 | 1 mM |
| P5 adaptor-ligation primer | 2 µM |
| P7 adaptor-ligation primer | 2 µM |
| pfx DNA polymerase | 2 U |
| DOP-PCR product template | as required |
| sterilized distilled water | up to desired volume |

The sequences of P5 adaptor-ligation primer and P7 adaptor-ligation primer were respectively:

```
P5 adaptor-ligation primer:
                                      (SEQ ID NO: 3)
AATGATACGGCGACCACCGAGATCTACACTCTTTCCCTACACGACGCTC

TTCCGATCT.

P7 adaptor-ligation primer:
CAAGCAGAAGACGGCATACGAGATXXXXXXGTGACTGGAGTTCAGACGT

GTGCTCTTCCGATCT.
```

Among each of the adaptor-ligation PCR amplification systems, the P5 adaptor-ligation primers were the same one, which was an adaptor sequence shown as SEQ ID NO: 3 in Illumina Hiseq2000 library construction, comprising binding Flowcell and sequencing adaptors.

The sequence of P7 adaptor-ligation primer as above-described, comprised an index sequence XXXXXX, and the index in each of the adaptor-ligation PCR reaction systems was mutually different. Besides, the last 13 bp of the P5 and P7 adaptor-ligation primer were consistent with the DOP-Amp primer.

In details, the P7 sequence of each adaptor-ligation PCR reaction system was shown below:

```
the P7 sequence of YH1 adaptor-ligation PCR
reaction system was:
                                      (SEQ ID NO: 4)
CAAGCAGAAGACGGCATACGAGATAAGCTAGTGACTGGAGTTCAGACGT

GTGCTCTTCCGATCT;

the P7 sequence of YH2 adaptor-ligation PCR
reaction system was:
                                      (SEQ ID NO: 5)
CAAGCAGAAGACGGCATACGAGATACATCGGTGACTGGAGTTCAGACGT

GTGCTCTTCCGATCT;

the P7 sequence of YH3 adaptor-ligation PCR
reaction system was:
                                      (SEQ ID NO: 6)
CAAGCAGAAGACGGCATACGAGATGCCTAAGTGACTGGAGTTCAGACGT

GTGCTCTTCCGATCT;

the P7 sequence of T21 adaptor-ligation PCR
reaction system was:
                                      (SEQ ID NO: 7)
CAAGCAGAAGACGGCATACGAGATTGGTCAGTGACTGGAGTTCAGACGT

GTGCTCTTCCGATCT,
``` in which in SEQ ID NO: 4-7, six nucleotides in bold and italic were the index sequence.

Then, in accordance with the reaction conditions shown in Table 5, each of the adaptor-ligation PCR reaction systems was respectively subjected to the adaptor-ligation PCR, to respectively obtain each of the third PCR amplification products, which respectively constituted the nucleic acid library of each sample: YH1 library, YH2 library, YH3 library and T21 library.

TABLE 5

| Temperature | Duration | Cycles |
| --- | --- | --- |
| 94~98° C. | 2~5 minutes | 1 |
| 94~98° C. | 15 seconds~2 minutes | 0~10 |
| 50~60° C. | 15 seconds~2 minutes | |
| 65~72° C. | 15 seconds~2 minutes | |
| 94~98° C. | 15 seconds~2 minutes | 5~20 |
| 58~65° C. | 15 seconds~2 minutes | |
| 65~72° C. | 15 seconds~2 minutes | |
| 4~12° C. | hold | |

Figure 3:
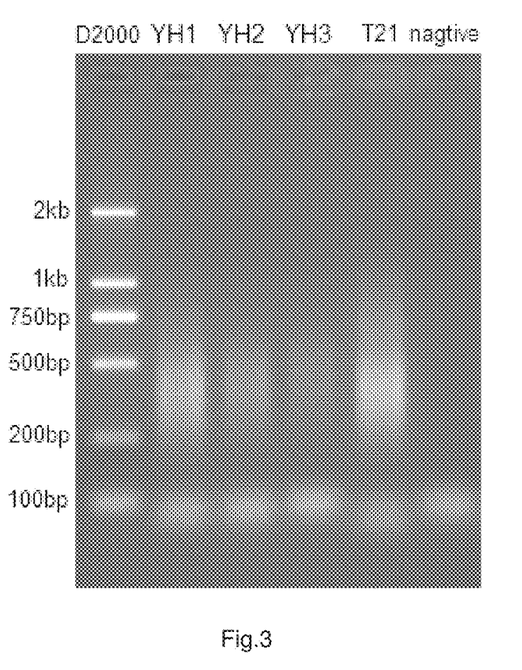
FIG. 3 shows an electrophoresis detection result of each adaptor-ligation PCR product when constructing a single cell genome DNA library by the method of constructing a nucleic acid library of the present disclosure, according to an embodiment of the present disclosure.

Each of the nucleic acid libraries above-described was subjected to electrophoresis detection, the result thereof was shown in FIG. 3. As can be seen from FIG. 3, lanes from left to right were respectively: Marker (D2000), YH1 library, YH2 library, YH3 library, T21 library and negative control.

6. Fragment Selection and Purification

The above-described nucleic acid libraries were the third PCR amplification product, all comprising an impurity such as primer dimer, and having a dispersed distribution of fragment size, which needed to be subjected to fragment selection and purification, specific steps were shown below:

An area in the gel corresponding to the DNA fragments having a length of 300 bp to 500 bp was cut off, and subjected to DNA fragment recycling and purification using QIAquick Gel Extraction Kit from Qiagen Company. Details referred to a specification provided by the kit.

Figure 4:
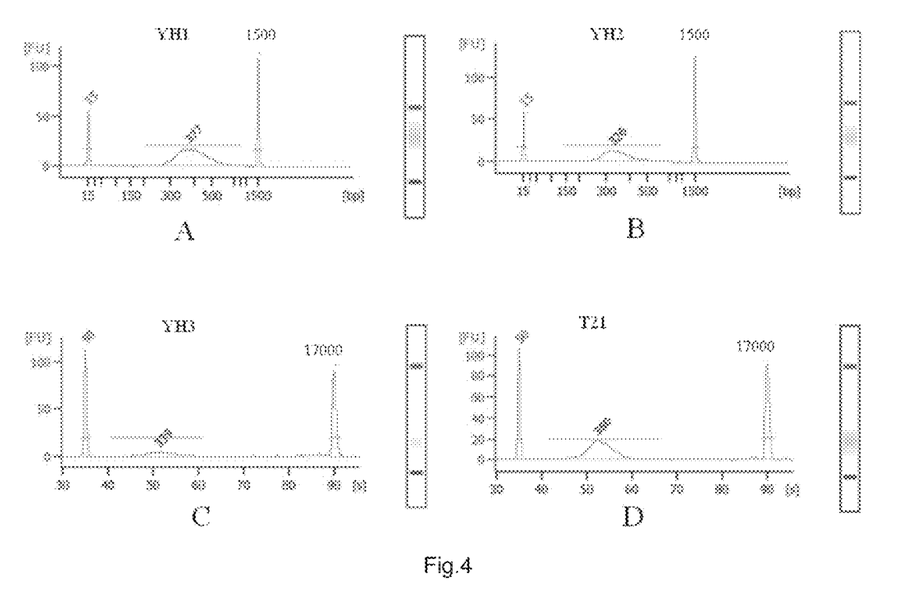

Then, each of the selected and purified nucleic acid libraries above-described was subjected to detection by Agilent 2100 bioanalyser, the detection result was shown in FIG. 4. As can be seen from FIG. 4 that, FIG. 4A showed a fragment detection result of YH1 sample with a desired major band located at 377 bp; FIG. 4B showed a fragment detection result of YH2 sample with a desired major band located at 326 bp; FIG. 4C showed a fragment detection result of YH3 sample with a desired major band located at 339 bp; and FIG. 4D showed a fragment detection result of T21 sample with a desired major band located at 360 bp; the above result indicated that the selected and purified fragments were qualified.

Therefore, 4 single cell genome DNA libraries deriving from single lymphocytic cell sample were obtained.

7. Illumina Hiseq2000 Sequencing

By means of Single-End sequencing, using one sequencing channel, each of the nucleic acid libraries obtained in above steps was simultaneously subjected to sequencing, with a read length of 50 bp. The statistical sequencing data was shown in Table 6.

TABLE 6

| Sample ID | Library ID | Number of Read | Aligning ratio (%) | Unique aligning ratio (%) |
|---|---|---|---|---|
| YH1 | YH1AADPPEI-1 | 20673324 (20.7M) | 93.86% | 89.80% |
| YH2 | YH2ABDPPEI-2 | 21352924 (21.4M) | 94.32% | 90.03% |
| YH3 | YH3ACDPPEI-3 | 21290934 (21.3M) | 93.46% | 89.61% |
| T21 | T21ADDPPEI-5 | 20980937 (21.0M) | 94.36% | 90.27% |

Furthermore, a ratio of each autosomal data volume to autosomal total data volume in 4 nucleic acid libraries were subjected to a statistical calculation, in which the number of reads was subjected to the statistical calculation, the result thereof was shown in Table 7.

TABLE 7

| Chromosome | YH1 | YH2 | YH3 | T21 |
|---|---|---|---|---|
| chr1 | 0.085 | 0.084 | 0.083 | 0.083 |
| chr2 | 0.096 | 0.094 | 0.093 | 0.093 |
| chr3 | 0.082 | 0.078 | 0.078 | 0.076 |
| chr4 | 0.079 | 0.079 | 0.076 | 0.075 |
| chr5 | 0.070 | 0.071 | 0.071 | 0.070 |
| chr6 | 0.071 | 0.067 | 0.069 | 0.068 |
| chr7 | 0.057 | 0.057 | 0.058 | 0.057 |
| chr8 | 0.057 | 0.054 | 0.058 | 0.056 |
| chr9 | 0.039 | 0.042 | 0.043 | 0.042 |
| chr10 | 0.047 | 0.046 | 0.045 | 0.046 |
| chr11 | 0.048 | 0.050 | 0.050 | 0.049 |
| chr12 | 0.048 | 0.049 | 0.051 | 0.049 |
| chr13 | 0.038 | 0.038 | 0.039 | 0.038 |
| chr14 | 0.031 | 0.034 | 0.034 | 0.034 |
| chr15 | 0.026 | 0.029 | 0.029 | 0.028 |
| chr16 | 0.025 | 0.023 | 0.023 | 0.024 |
| chr17 | 0.021 | 0.021 | 0.021 | 0.021 |
| chr18 | 0.029 | 0.031 | 0.028 | 0.029 |
| chr19 | 0.011 | 0.011 | 0.011 | 0.012 |
| chr20 | 0.019 | 0.020 | 0.020 | 0.020 |
| chr21 | 0.013 | 0.013 | 0.014 | 0.020 |
| chr22 | 0.008 | 0.008 | 0.008 | 0.008 |

As shown in Table 7, the sequencing result of T21 library showed that the data volume ratio of chromosome 21 in T21 library was obviously higher than that of YH single cell (YH1, YH2, YH3, which were normal karyotypes), with a ratio of T21 to YH being approximately to 3:2. The statistical result indicted that the method of constructing a nucleic acid library of the present disclosure may be used to effectively construct single cell genome DNA library, and the obtained single cell genome DNA library could be effectively used in detection of chromosome number variation.

Example 2

The nucleic acid libraries were constructed using the method in EXAMPLE 1, the difference was the reactions condition for the DOP-PCR amplification, which were shown in Table 8:

TABLE 8

| Temperature | Duration | Cycles |
|---|---|---|
| 94~98° C. | 2~5 minutes | 1 |
| 94~98° C. | 15 seconds~2 minutes | 5~25 |
| 10~19° C. | 20 seconds~5 minutes | |
| 20~30° C. | 20 seconds~5 minutes | |
| 31~40° C. | 20 seconds~5 minutes | |
| 65~72° C. | 15 seconds~3 minutes | |
| 4~12° C. | hold | |

The result of the present example indicated that, the reaction condition for the DOP-PCR amplification of the present example could also be used to achieve the purpose of constructing nucleic acid library which could be used in the subsequent sequencing.

Example 3

Constructing of a Nucleic Acid Library with a Trace Amount of DNA/cDNA Sample

The samples of the present example is a trace amount of DNA/cDNA sample, which were respectively a trace amount of genome DNA, IP product DNA, plasma DNA, and cDNA product from reverse transcription with RNA. Among them, the samples of IP product DNA, plasma DNA, and genome DNA needed a 5-fold gradient dilution, respectively with an initial amount of 200 pg, 40 pg, and 8 pg for library constructing. cDNA sample was obtained from reverse transcription with 1 μg total RNA (mouse) using six nucleotides random primer and Superscript II reverse transcriptase, and then the cDNA sample was subjected to a 5-fold gradient dilution to obtain 4 initial amounts of original concentration, $5^{-1}$, $5^{-2}$, and $5^{-3}$ for library constructing.

The present example used the method of constructing a nucleic acid library of the present disclosure, in accordance to following steps, to respectively construct nucleic acid libraries with each of DNA/cDNA samples.

1. DOP-PCR Amplification

A DOP reaction system of each trace amount of DNA/cDNA samples was respectively prepared in accordance with the ratio shown in Table 9.

TABLE 9

| Components | Final Concentration |
|---|---|
| 10 x Pfx amplification buffer | 2 x |
| 10 x Enhancer Solution | 1 x |
| 10 mM dNTP mixed buffer | 0.5 mM of each |
| 50 mM MgSO$_4$ | 1 mM |
| DOP primer | 0.8 μM |
| pfx DNA polymerase | 2 U |
| a trace amount of DNA/cDNA | as required |
| sterilized distilled water | up to desired volume |

When comparing the DOP reaction system, each of the above described components in Table 9 would be mixed and covered with an appropriate mineral oil; and after covered with a cap thereof, the PCR tubes were subjected to an instant centrifuging.

Then, in accordance with the reaction conditions shown in Table 10, each of the DOP reaction system obtained by the above described preparation was subjected to a DOP-PCR amplifying, to obtain a first PCR amplification product.

TABLE 10

| Temperature | Duration | Cycles |
|---|---|---|
| 95° C. | 5 minutes | 1 |
| 95° C. | 1 minutes | 1~5 |
| 15° C. | 20 minutes | |
| 25° C. | 20 minutes | |
| 35° C. | 20 minutes | |
| 68° C. | 1 minutes | |
| 4° C. | hold | |

2. Second Amplifying

The DOP-Amp primer was respectively added into the each DOP reaction systems obtained from the DOP-PCR amplification, to reach a final concentration of 0.4 μM, so as to respectively obtain each second PCR amplification reaction system.

Then, in accordance with the reaction conditions shown in Table 10, each of the second PCR amplification reaction system was subjected to a second amplification, to obtain a second PCR amplification product.

TABLE 11

| Temperature | Duration | Cycles |
|---|---|---|
| 95° C. | 5 minutes | 1 |
| 95° C. | 1 minutes | 15~20 |
| 54° C. | 30 seconds | |
| 68° C. | 30 seconds~1 minutes | |
| 4° C. | hold | |

Then, the above obtained second PCR amplification products were subjected to electrophoresis and concentration assay, the qualified products were preserved for use.

3. Adaptor-Ligation PCR

In accordance with the ratio shown in Table 12, an adaptor-ligation PCR reaction system of each second PCR amplification product obtained in step 4 was prepared respectively. The used DNA polymerase is a thermo-tolerant DNA polymerase pfx enzyme.

TABLE 12

| Components | Final Concentration |
|---|---|
| 10 x Pfx Amplification Buffer | 2 x |
| 10 x Enhancer Solution | 1 x |
| 10 mM dNTP mixed buffer | 0.5 mM of each |
| 50 mM MgSO$_4$ | 1 mM |
| P5 adaptor-ligation primer | 0.4 μM |
| P7 adaptor-ligation primer | 0.4 μM |
| pfx DNA polymerase | 1 U |
| DOP-PCR product template | 10 μL |
| sterilized distilled water | up to desired volume |

The sequences of P5 adaptor-ligation primer in Table 12 had a same sequence with the P5 adaptor-ligation primer in EXAMPLE 1.

P7 adaptor-ligation primer of each adaptor-ligation PCR reaction system was:

P7 adaptor-ligation primer of each adaptor-ligation PCR reaction system for IP product DNA sample was:

(SEQ ID NO: 4)
CAAGCAGAAGACGGCATACGAGATAAGCTAGTGACTGGAGTTCAGACGT

GTGCTCTTCCGATCT;

P7 adaptor-ligation primer of each adaptor-ligation PCR reaction system for plasma DNA sample was:

(SEQ ID NO: 5)
CAAGCAGAAGACGGCATACGAGATACATCGGTGACTGGAGTTCAGACGT

GTGCTCTTCCGATCT;

P7 adaptor-ligation primer of each adaptor-ligation PCR reaction system for cDNA sample was:

(SEQ ID NO: 6)
CAAGCAGAAGACGGCATACGAGATGCCTAAGTGACTGGAGTTCAGACGT

GTGCTCTTCCGATCT;

P7 adaptor-ligation primer of each adaptor-ligation PCR reaction system for genome DNA (gDNA) was:

(SEQ ID NO: 7)
CAAGCAGAAGACGGCATACGAGATTGGTCAGTGACTGGAGTTCAGACGT

GTGCTCTTCCGATCT, in which in SEQ ID NO: 4-7, six nucleotides in bold and italic were the index sequence.

Then, in accordance with the reaction conditions shown in Table 13, each of the adaptor-ligation PCR reaction systems was respectively subjected to the adaptor-ligation PCR, to respectively obtain each of the third PCR amplification products, which respectively constituted the nucleic acid library of each sample.

TABLE 13

| Temperature | Duration | Cycles |
|---|---|---|
| 95° C. | 5 minutes | 1 |
| 95° C. | 1 minutes | 3~10 |
| 54° C. | 30 seconds | |
| 68° C. | 30 seconds~1 minutes | |
| 95° C. | 1 minutes | 5~10 |
| 62° C. | 30 seconds | |
| 68° C. | 30 seconds~1 minutes | |
| 4° C. | hold | |

Figure 5:
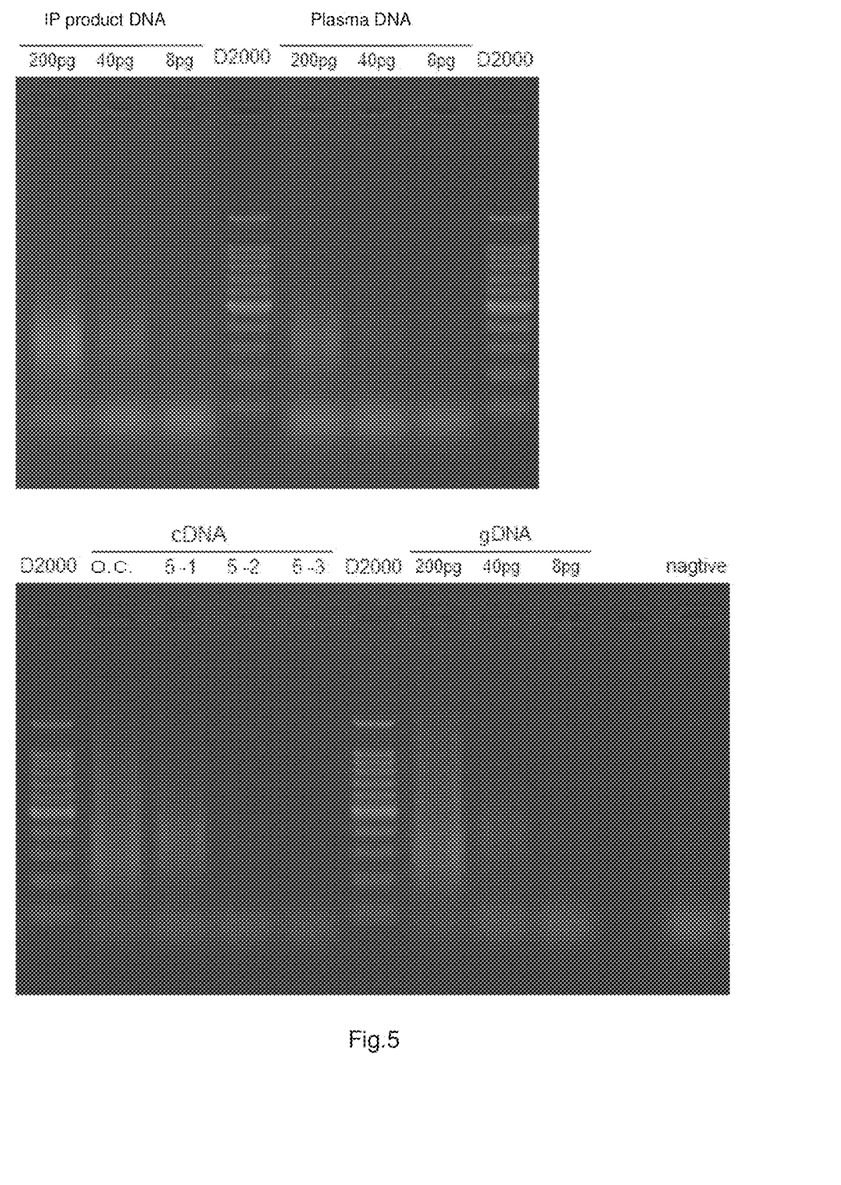
FIG. 5 is an electrophoresis detection result of each adaptor-ligation PCR product, when constructing a nucleic acid library with a trace amount of nucleic acid sample (IP product DNA, plasma DNA, cDNA, gDNA) by the method of constructing a nucleic acid library of the present disclosure, according to an embodiment of the present disclosure.

Each of the nucleic acid libraries above-described was subjected to electrophoresis detection, the result thereof was shown in FIG. 5. As can be seen from FIG. 5, lanes from left to right in upper panel were respectively: nucleic acid libraries constructed with IP product DNA samples respectively having initial amounts of 200 pg, 40 pg, and 8 pg, Marker (D2000), nucleic acid libraries constructed with Plasma DNA samples respectively having initial amounts of 200 pg, 40 pg, and 8 pg, Marker (D2000); lanes from left to right in lower panel were respectively: Marker (D2000), nucleic acid libraries constructed with cDNA samples having initial amounts of original concentration, $5^{-1}$, $5^{-2}$, and $5^{-3}$, Marker (D2000), nucleic acid libraries constructed with gDNA samples having initial amounts of 200 pg, 40 pg, and 8 pg, negative control.

FIG. 5 indicated that the present example successfully constructed nucleic acid libraries with 4 kinds of trace amount of DNA/cDNA samples.

5. Fragment Selection and Purification

In accordance with following steps, each of the nucleic acid libraries above-described was subjected to the fragment selection and purification: An area in the gel corresponding to the DNA fragments having a length of 200 bp to 500 bp was cut off, and subjected to DNA fragment recycling and purification using QIAquick Gel Extraction Kit from Qiagen Company. Details referred to a specification provided by the kit.

Figure 6:
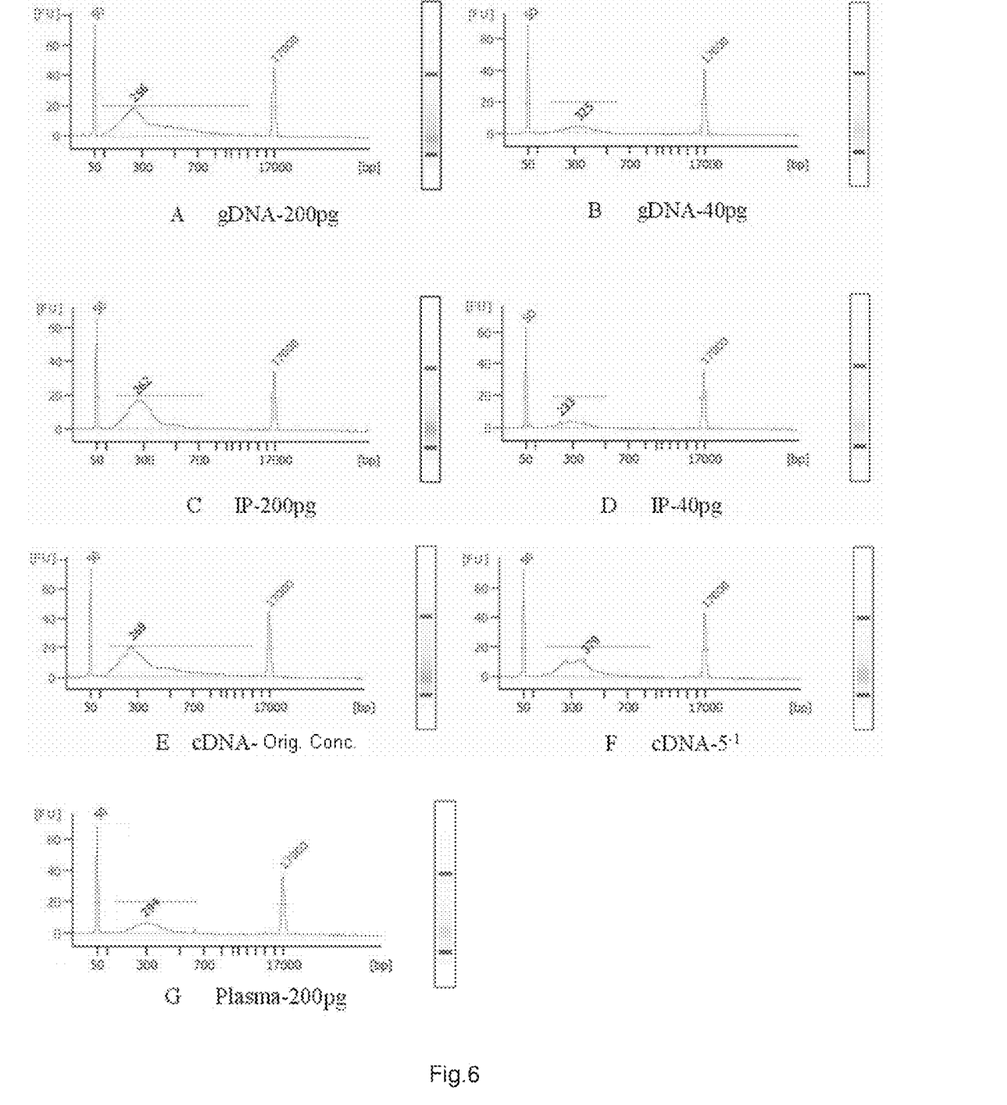

Then, each of the selected and purified nucleic acid libraries above-described was subjected to detection by Agilent 2100 bioanalyser, the detection result was shown in FIG. 6. As can be seen from FIG. 6 that, FIG. 6A showed a fragment detection result with a trace amount 200 pg of genome DNA, FIG. 6B showed a fragment detection result with a trace amount 40 pg of genome DNA, FIG. 6C showed a fragment detection result with 200 pg of IP product DNA, FIG. 6D showed a fragment detection result with 40 pg of IP product DNA, FIG. 6E showed a fragment detection result of cDNA with the original concentration (abbreviating as O.C.), FIG. 6F showed a fragment detection result of cDNA-$5^{-1}$, FIG. 6G showed a fragment detection result of 200 pg of plasma DNA.

Then, nucleic acid libraries constructed with 4 kinds of a trace amount of DNA/cDNA samples were obtained.

Then, each of the constructed nucleic acid libraries obtained according to above described steps was subjected to sequencing by means of the sequencing method in EXAMPLE 1. The obtained sequencing result indicated that the method of constructing a nucleic acid library of the present disclosure could be effectively used in constructing the nucleic acid libraries with a trace amount of DNA/cDNA sample, and the constructed nucleic acid libraries could be used for detection and diagnosis of diseases.

Example 4

Kit

A kit for constructing a library with a single cell or a trace amount of nucleic acid sample comprised following components:

(1) a DOP primer provided in a first container;
(2) a DOP-Amp primer provided in a second container;
(3) an adaptor-ligation primer provided in a third container;
(4) a reagent required for required for DOP-PCR amplification provided in a fourth container;
(5) a reagent for nucleic acid purification provided in a fifth container;
(6) a flow cell for high-throughput sequencing provided in a sixth container;
(7) a specification.

INDUSTRIAL APPLICABILITY

The method of constructing a nucleic acid library, the method of determining a nucleotide sequence of a nucleic acid sample and a kit of the present disclosure, may be effectively used in constructing a nucleic acid library with a single cell or a trace amount of nucleic acid sample, and sequencing the obtained nucleic acid library, with characteristics of high sensitivity, high accuracy, and good repeatability, which may be effectively used in detection and diagnosis of diseases.

Reference throughout this specification to "an embodiment," "some embodiments," "one embodiment", "another example," "an example," "a specific examples," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example, "in an example," "in a specific examples," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by those skilled in the art that the above embodiments cannot be construed to limit the present disclosure, and changes, alternatives, and modifications can be made in the embodiments without departing from spirit, principles and scope of the present disclosure.

What is claimed is:

1. A method of constructing a nucleic acid library, comprising following steps of:

subjecting a nucleic acid sample to a first PCR amplification using a DOP primer, to obtain a first PCR amplification product;

subjecting the first PCR amplification product to a second PCR amplification using a DOP-Amp primer, to obtain a second PCR amplification product; and subjecting the second PCR amplification product to an adaptor-ligation PCR using a first and second adaptor-ligation primer, to obtain a third PCR amplification product, wherein the third PCR amplification product constitutes the nucleic acid library, and wherein the DOP primer at least has a non-degenerate nucleotide region located at the 5'-end of the DOP primer and a degenerate nucleotide region downstream thereof, wherein the DOP primer has a sequence shown as SEQ ID NO: 1, wherein the DOP-Amp primer is homologous or substantially homologous to the non-degenerate oligonucleotide region located at the 5'-end of the DOP primer, wherein the 3' end of the adaptor-ligation primers has a nucleotide sequence matching with the DOP-Amp primer; and wherein the first adaptor-ligation primer comprises P5 and the second adaptor-ligation primer comprises P7.

2. The method of claim 1, wherein the nucleic acid sample has a nucleic acid content of 2 pg to 1 µg.

3. The method of claim 1, further comprising a step of:
subjecting the third PCR amplification product to a fragment selection, to obtain selected fragments,
wherein the selected fragments have a length of 100 to 1000 bp.

4. The method of claim 1, wherein the nucleic acid sample derives from 1 to 200 single cells.

5. The method of claim 1, wherein the nucleic acid sample is at least one selected from a trace amount of genome DNA, immune-precipitation product DNA, plasma DNA and cDNA.

6. The method of claim 1, wherein the nucleic acid sample derives from at least one selected from a group consisting of environment, body fluid and excreta.

7. The method of claim 1, wherein the nucleic acid sample is subjected to the first PCR amplification using a DOP primer, wherein the DOP primer comprises:

a non-degenerate oligonucleotide region located at the 5'-end of the DOP primer;

a degenerate oligonucleotide region located in the middle of the DOP primer; and an anchor region located at the 3'-end of the DOP primer, wherein the anchor region located at the 3'-end of the DOP primer has a nucleotide sequence of at least one selected from TG, TGTGG and GTCT, and wherein the non-degenerate oligonucleotide region located at the 5'-end of the DOP primer has a nucleotide sequence shown as SEQ ID NO: 2.

8. The method of claim 1, wherein the nucleic acid sample is subjected to the first PCR amplification using a DOP primer, wherein the DOP primer comprises:

a non-degenerate oligonucleotide region located at the 5'-end of the DOP primer; and a degenerate oligonucleotide region located in the middle of the DOP primer and at the 3'-end of the DOP primer, and wherein the non-degenerate oligonucleotide region located at the 5'-end of the DOP primer has a nucleotide sequence shown as SEQ ID NO: 2.

9. A method of determining a nucleotide sequence of a nucleic acid sample, comprising:
constructing a nucleic acid library with the nucleic acid sample using the method according to claim 1; and
subjecting the nucleic acid library to sequencing and data analysis, to determine the nucleotide sequence of the nucleic acid sample.

10. The method of claim 9, wherein the nucleic acid sample is at least one selected from a single cell and a trace amount of nucleic acid sample.

* * * * *

SEQUENCE LISTING

```
<160> NUMBER OF SEQ ID NOS: 7

<210> SEQ ID NO 1
<211> LENGTH: 23
<212> TYPE: DNA
<213> ORGANISM: Artificial
<220> FEATURE:
<223> OTHER INFORMATION: DOP primer
<220> FEATURE:
<221> NAME/KEY: misc_feature
<222> LOCATION: (14)..(23)
<223> OTHER INFORMATION: n is a, c, g, or t

<400> SEQUENCE: 1
gctcttccga tctnnnnnnn nnn                                   23

<210> SEQ ID NO 2
<211> LENGTH: 13
<212> TYPE: DNA
<213> ORGANISM: Artificial
<220> FEATURE:
<223> OTHER INFORMATION: DOP-Amp primer
```

```
<400> SEQUENCE: 2
gctcttccga tct                                                      13

<210> SEQ ID NO 3
<211> LENGTH: 58
<212> TYPE: DNA
<213> ORGANISM: Artificial
<220> FEATURE:
<223> OTHER INFORMATION: P5 adaptor-ligation primer

<400> SEQUENCE: 3
aatgatacgg cgaccaccga gatctacact ctttccctac acgacgctct tccgatct     58

<210> SEQ ID NO 4
<211> LENGTH: 64
<212> TYPE: DNA
<213> ORGANISM: Artificial
<220> FEATURE:
<223> OTHER INFORMATION: P7 adaptor-ligation primer

<400> SEQUENCE: 4
caagcagaag acggcatacg agataagcta gtgactggag ttcagacgtg tgctcttccg   60
atct                                                                64

<210> SEQ ID NO 5
<211> LENGTH: 64
<212> TYPE: DNA
<213> ORGANISM: Artificial
<220> FEATURE:
<223> OTHER INFORMATION: P7 adaptor-ligation primer

<400> SEQUENCE: 5
caagcagaag acggcatacg agatacatcg gtgactggag ttcagacgtg tgctcttccg   60
atct                                                                64

<210> SEQ ID NO 6
<211> LENGTH: 64
<212> TYPE: DNA
<213> ORGANISM: Artificial
<220> FEATURE:
<223> OTHER INFORMATION: P7 adaptor-ligation primer

<400> SEQUENCE: 6
caagcagaag acggcatacg agatgcctaa gtgactggag ttcagacgtg tgctcttccg   60
atct                                                                64

<210> SEQ ID NO 7
<211> LENGTH: 64
<212> TYPE: DNA
<213> ORGANISM: Artificial
<220> FEATURE:
<223> OTHER INFORMATION: P7 adaptor-ligation primer

<400> SEQUENCE: 7
caagcagaag acggcatacg agattggtca gtgactggag ttcagacgtg tgctcttccg   60
atct                                                                64
```